United States Patent [19]
Pan et al.

[11] Patent Number: 5,363,458
[45] Date of Patent: Nov. 8, 1994

[54] FIBER OPTIC LIGHT DIFFUSER

[75] Inventors: Anpei Pan, North Plainfield; Dipak Biswas, Plainsboro, both of N.J.

[73] Assignee: Fiber guide Industries, Stirling, N.J.

[21] Appl. No.: 203,328

[22] Filed: Feb. 28, 1994

[51] Int. Cl.$^5$ .............................................. G02B 23/26
[52] U.S. Cl. ........................................ 385/31; 385/36; 385/128; 385/901; 385/902
[58] Field of Search ....................... 385/31, 33, 36, 38, 385/901, 902, 126, 127, 128; 362/32

[56] References Cited

U.S. PATENT DOCUMENTS

| | | | |
|---|---|---|---|
| 2,589,569 | 3/1952 | Peter et al. | 385/901 |
| 3,498,692 | 3/1970 | Jewitt et al. | 385/901 |
| 4,660,925 | 4/1987 | McCaughan, Jr. | 362/32 |
| 5,074,632 | 12/1991 | Potter | 385/31 |
| 5,119,461 | 6/1992 | Beyer et al. | 385/147 |
| 5,168,538 | 12/1992 | Gillespie | 385/123 |
| 5,276,693 | 1/1994 | Long et al. | 372/6 |
| 5,303,324 | 4/1994 | Lundahl | 385/147 |

*Primary Examiner*—Frank Gonzalez
*Attorney, Agent, or Firm*—Herbert M. Shapiro

[57] ABSTRACT

Heat and light generating, fiber optic, cylindrical diffusers are structured to operate more efficiently and with increased uniformity by the inclusion of rings of prescribed indicies of refraction about the unclad distal end portion of the diffuser. Such a diffuser also includes a conical distal tip. A sealed Teflon (TM) sleeve containing diffusing material in place over the entire length of the diffuser also improves the uniformity of heat distribution.

9 Claims, 2 Drawing Sheets

FIBER OPTIC LIGHT DIFFUSER

FIELD OF THE INVENTION

This invention relates to fiber optic diffusers and more particularly to such diffusers useful for generating uniform heat in human or animal tissue at the distal end thereof.

BACKGROUND OF THE INVENTION

Fiber optic diffusers are well known in the art. Such diffusers are structured for two quite different classes of procedures within the human body. The first of these procedures is a light diffuser for promoting photochemical reactions within the body.

The generally accepted term for procedures employing light diffusers for use in promoting photochemical reactions is "Photodynamic Therapy" (PDT). Such procedures are the primary procedures for treating cancer in humans or animals. One type of diffuser useful in PDT is the cylindrical diffuser or "line Source".

A fiber optic cylindrical diffuser is characterized by a cylindrical light scattering pattern symmetrical with respect to the central axis of the optical fiber. Such apparatus has been made with an optical fiber having an exposed core portion at one end with a scattering medium coated on the exposed portion.

The apparatus also includes a tube attached to the sleeve covering the clad portion of the fiber adjacent the unclad portion. Copending application Ser. No. 08/007,112, filed Jan. 21, 1993 (now allowed) and assigned to the assignee of the present application describes one such cylindrical diffuser for PDT.

The second class of procedures employing the general structure of a cylindrical diffuser distributes uniform light that generates heat at the distal end of the fiber. Such apparatus is employed, for example, to provide a heat delivering probe for prostate surgery. The present invention is directed at providing an improved diffuser for the generation of a uniform light distribution profile that generates uniform heat in the human or animal tissue.

BRIEF DESCRIPTION OF ILLUSTRATIVE EMBODIMENTS OF THIS INVENTION

In accordance with the principles of this invention, a cylindrical diffuser for uniform heat generation includes a conical distal end at the unclad portion of the fiber as described in the above-mentioned patent application. In addition, the diffuser includes at least one ring of relatively low index of refraction material around the unclad portion near the base of the unclad portion where that portion joins the clad portion. In other embodiments, several rings of the same low index of refraction material or of differing indicies of refraction are spaced along the unclad portion of the fiber for reducing, or tailoring the emission profile of, the amount of light exiting the fiber before the light reaches the distal end of the fiber.

DETAILED DESCRIPTION OF ILLUSTRATIVE EMBODIMENTS OF THIS INVENTION

Figure 1:
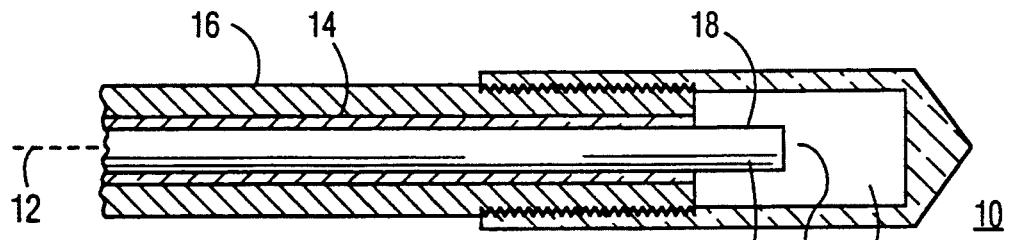
FIG. 1 is an enlarged cross sectional view of a prior art cylindrical diffuser.

FIG. 1 shows an enlarged cross section of a prior art PDT diffuser 10. The diffuser includes an optical fiber 11 having a proximal end 12 and a distal end 13. The fiber includes a cladding layer 14 and a sheathing layer 16. The cladding and sheathing layers are stripped off of the fiber at the distal end leaving the fiber core exposed as shown at 18. The exposed fiber core is coated with a layer of scattering material.

Figure 2:
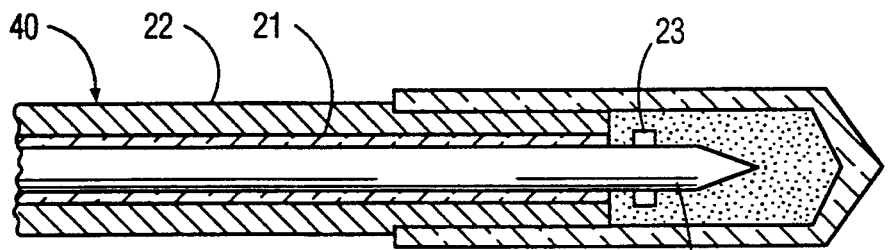
FIG. 2 is an enlarged cross sectional view of a heat generating diffuser in accordance with the principles of this invention.

FIG. 2 shows an enlarged cross section of a cylindrical diffuser in accordance with the principles of this invention adapted for uniform heat generation. The diffuser, in this instance, also includes an optical fiber core 20 having the clad and sheathing layers 21 and 22 removed leaving the distal end of the fiber unclad as shown. But in the embodiment of FIG. 2, a ring 23 of a material having a relatively low index of refraction, is present to at least partially reflect, back into the fiber, light which otherwise would exit the fiber as the light is being transmitted along the fiber core. In this manner, a more even distribution of light is obtained. This reflects even distribution of heat in the tissue at the distal end of the diffuser. A suitable material for the ring is Silvue (TM) and has a thickness of from ten to one hundred microns and a width of from one to five millimeters.

Figure 3:
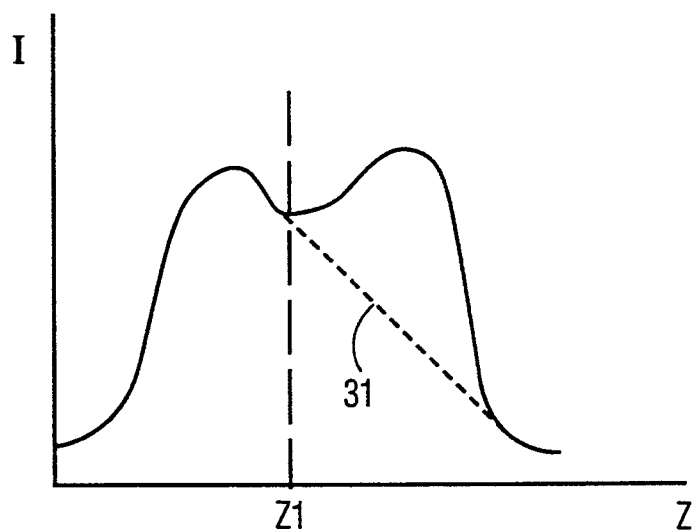
FIG. 3 is a graph showing the heat generating profiles for the diffusers of FIGS. 1 and 2.

FIG. 3 is a graph of light intensity I plotted as a function of distance Z along the exposed fiber core end as shown in FIG. 2. The light intensity is reduced at a point Z1 corresponding to the position of ring 23 thus indicating that light is reflected back into the core by the ring. In the absence of a ring, the light intensity peaks and then reduces as indicated by the broken curve 31 which represents the light distribution from the diffuser of FIG. 1.

Figure 4:
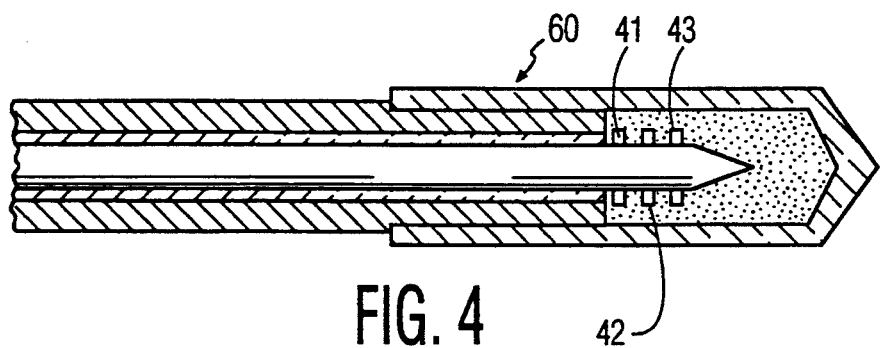
FIGS. 4 and 5 are cross sectional views of alternative embodiments in accordance with the principles of this invention.
Figure 5:
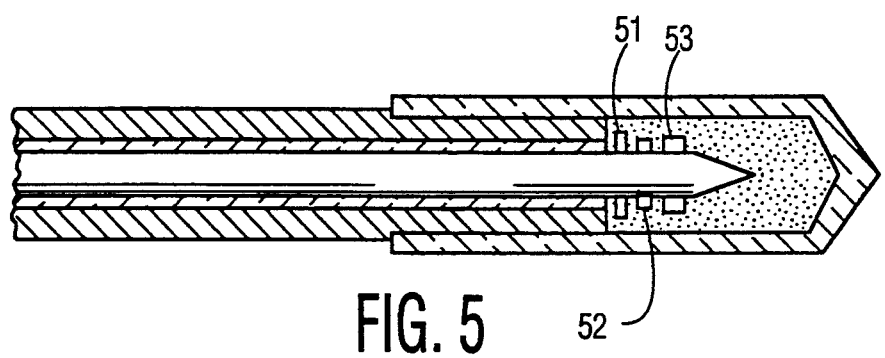
Figure 6:
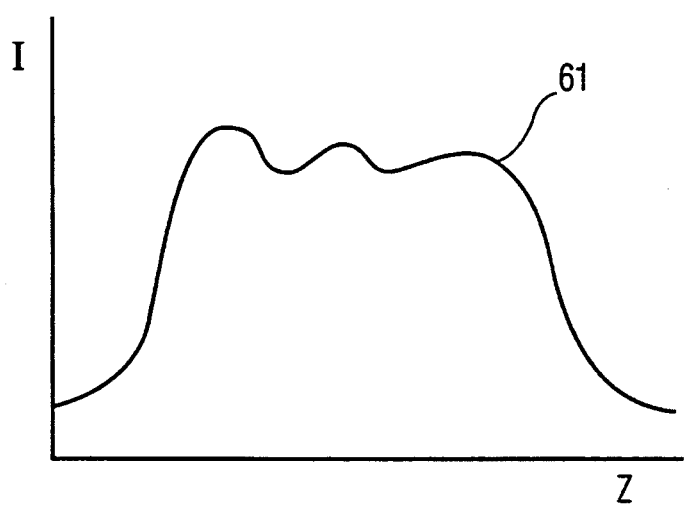
FIG. 6 is a graph of the emission profiles of the embodiments of FIGS. 4 and 5.

The exposed fiber core tip may include a plurality of rings 41, 42, and 43 like ring 23 of FIG. 2. The rings are shown in FIG. 4 as being of like thickness, width and spacing and of the same material with the same relatively low index of refraction. FIG. 5 illustrates the embodiment in which rings 51, 52, and, 53 comprise different materials with different indicies of refraction and have different thicknesses, widths and spacings useful in tailoring the light (or heat) distribution profile to provide any desired heat or light distribution. For illustration purposes, the rings of FIG. 5 may comprise Silvue (TM) and Epoxy materials having thicknesses of ten, fifteen and twenty microns with widths of one, three, and five millimeters and spacings of two three and four millimeters. FIG. 6 shows a graph of intensity plotted against distance along the unclad portion of the fiber of the embodiment of FIG. 5. The curve, 61, shows the recesses in the light profile which correspond to the positions of the rings.

The various dimensions herein are stated in the context of a Quartz optical fiber having a diameter of 600 microns with a transparant polymer layer of between ten and 20 microns thick and a Tefzel(TM) or Teflon (TM) sheathing having an outer diameter of about 860 microns. In use, the fiber is connected at the proximal end to an SMA style connector (not shown) to the output of a laser. The scattering medium comprises an optical adhesive such as a silicone polymer and a powdered scatterer such as powdered synthetic Sapphire (Aluminum Oxide), diamond dust or Titanium oxide dust. The scattering medium is contained inside a Teflon (TM) sleeve and placed over the unclad portion of the fiber and over the Teflon (TM) or Tefzel (TM) sheathing. The distal end of the sleeve is sealed.

The first ring in any of the embodiments herein may be placed contiguous to the termination of the cladding and sheathing layers as shown only in FIG. 4.

All the embodiments of FIGS. 2, 4, and 5 conveniently use Teflon (TM) sleeves, shown only in FIG. 4 as sleeve 60. The unclad fiber core at the distal end of the fiber is typically between one and two and one half centimeters long.

Diffusers of the type shown in FIGS. 2, 4, and 5 have been shown to deliver, at the distal end of the fiber, five to ten watts of input power per centimeter, greater than that obtained with prior art diffusers and with a much more uniform (or controlled) light or heat distribution profile. Clearly, transmission and power handling capabilities have been shown to be higher than that shown by prior art devices.

What is claimed is:

1. A cylindrical diffuser comprising an optical fiber having a proximal and a distal end, said fiber including a cladding for reflecting light back into said fiber and a protective sheath thereabout, said fiber including a distal end portion from which said cladding and said sheath are removed, said distal end portion including a ring of a material to reflect light back into said portion for providing a relatively even distribution of light and thus even distribution of heat in human or animal tissue at said distal end portion said diffuser including a sleeve enclosing said distal end portion and connecting to said clad portion, said sleeve and said distal end portion having conical shapes.

2. A diffuser as set forth in claim 1 including a plurality of rings spaced apart from one another along said distal end portion.

3. A diffuser as set forth in claim 2 wherein said rings are of relatively low index of refraction material.

4. A diffuser as set forth in claim 2 wherein said rings are of equal thicknesses, widths and spacings.

5. A diffuser as set forth in claim 4 wherein said rings are of relatively low like indicies of refraction.

6. A diffuser as set forth in claim 4 wherein said rings are of materials with different indicies of refraction.

7. A diffuser as set forth in claim 2 wherein said rings are of different thicknesses, widths and spacings.

8. A diffuser as set forth in claim 2 wherein said sheath comprises Teflon (TM) and includes a sleeve attached to said sheath and forming a chamber around said distal end portion, said chamber including light scattering material.

9. A diffuser as set forth in claim 3 wherein said rings comprise different materials from one another.

* * * * *